(12) United States Patent
Belardinelli et al.

(10) Patent No.: US 9,126,989 B2
(45) Date of Patent: *Sep. 8, 2015

(54) COMPOUND AND METHODS FOR TREATING LONG QT SYNDROME

(71) Applicant: Gilead Sciences, Inc., Foster City, CA (US)

(72) Inventors: Luiz Belardinelli, Palo Alto, CA (US); Sridharan Rajamani, Newark, CA (US); Dewan Zeng, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/448,307

(22) Filed: Jul. 31, 2014

(65) Prior Publication Data

US 2015/0038489 A1    Feb. 5, 2015

Related U.S. Application Data

(60) Provisional application No. 61/900,235, filed on Nov. 5, 2013, provisional application No. 61/861,344, filed on Aug. 1, 2013.

(51) Int. Cl.
*A61K 31/553* (2006.01)
*C07D 413/06* (2006.01)
*A61K 31/506* (2006.01)

(52) U.S. Cl.
CPC ............ *C07D 413/06* (2013.01); *A61K 31/506* (2013.01)

(58) Field of Classification Search
CPC .................................................... A61K 31/553
See application file for complete search history.

(56) References Cited

FOREIGN PATENT DOCUMENTS

WO    WO-03086401 A1    10/2003
WO    WO-2013/006485 A1    1/2013

OTHER PUBLICATIONS

Farzaneh-Far et al. (2013) "Anti-Ischemic Effect of Ranolazine Closely Parallels its QTC-Shortening Effect in Patients with Long-QT Syndrome 3" *Journal of the American College of Cardiology* 61(10) 61176-6 Abstract.
Goldenberg et al. (2008) "Long QT Syndrome" *Current Problems in Cardiology* 33: 629-694.
Moss et al. (2008) "Ranolazine Shortens Repolarization in Patients with Sustained Inward Sodium Current Due to Type-3 Long-QT Syndrome" *Journal of Cardiovascular Electrophysiology* 9(12):1289-1293.
International Search Report for PCT/US2014/049155, International Filing Date Jul. 31, 2014, mailed Oct. 17, 2014.

*Primary Examiner* — Bruck Kifle
(74) *Attorney, Agent, or Firm* — Francis O. Ginah

(57) ABSTRACT

Described herein is a method of treating long QT syndrome by administration of an effective amount of a potent and selective late sodium ion channel blocker.

14 Claims, 8 Drawing Sheets

COMPOUND AND METHODS FOR TREATING LONG QT SYNDROME

CROSS-REFERENCE TO RELATED APPLICATIONS

This application claims benefit under 35 U.S.C. §119(e) to U.S. Provisional Application Ser. No. 61/861,344, filed on Aug. 1, 2013 and Provisional Application Ser. No. 61/900,235, filed Nov. 5, 2013, the entirety of which are incorporated herein by reference.

FIELD

The present disclosure relates to a method of treating long QT syndrome by administration of an effective amount of a potent and selective late sodium ion channel blocker.

BACKGROUND

The congenital long QT syndrome (LQTS) is a clinically heterogenous group of inherited cardiac channelopathies characterized by prolongation of the electrocardiographic QTc interval and an increased propensity towards syncope, cardiac arrest, and sudden cardiac death (SCD) resulting from a unique form of polymorphic ventricular tachycardia (VT) known as torsades de pointer (TdP).

There are currently 13 putative subtypes of LQTS. The most common subtypes are LQT1 (~45%), LQT2 (~45%), and LQT3 (7%). Other forms of LQTS (LQT4-10) are very rare and account for <3% of all LQTS. LQT1 and LQT2 are caused by loss of function mutations in the genes encoding the potassium ($K^+$) channels that underlie the delayed rectifier $K^+$ currents, $I_{Ks}$ and $I_{Kr}$, respectively. LQT3 is caused by gain-of-function mutations in SCN5A, the gene that encodes the cardiac voltage-gated sodium ($Na^+$) channel, $Na_v1.5$, resulting in an increase in the late $Na^+$ current ($I_{Na}$).

The mutant gene causes abnormal channels to be formed and as these channels do not function properly, the electrical recovery of the heart takes longer, which manifests itself as a prolonged QT interval. For example, an inherited deletion of amino-acid residues 1505-1507 (KPQ) in the cardiac $Na^+$ channel, encoded by SCN5A, causes the severe autosomal dominant LQT3 syndrome associated with fatal ventricular arrhythmias. Fatal arrhythmias occur in 64% of LQT3 patients during sleep or rest, presumably because excess late $Na^+$ current abnormally prolongs repolarization, particularly at low heart rates and thereby favors development of early afterdepolarizations (EADs) and ectopic beats. Preferential slowing of repolarization in the mid-myocardium might further enhance transmural dispersion of repolarization and cause unidirectional block and reentrant arrhythmias. In another 16% of LQT3 patients, fatal cardiac events are triggered by exercise or emotion.

To date, approximately 75 distinct mutations in SCN5A have been linked to LQT3. In most of these mutations, incomplete or slow inactivation of sodium channels induces a persistent or "late" $Na^+$ current. At the myocyte level, the increased late $Na^+$ current prolongs the APD, and promotes the formation of EADs and DADs, which are cellular triggers for malignant arrhythmias. These molecular defects and altered kinetics in the sodium channel gating mechanism are characterized at the organ level by prolongation of the QTc interval. In patients with LQT3, QTc prolongation represents the electrocardiographic hallmark of prolonged ventricular repolarization due to increased late $Na^+$ current. Finally, at the whole organism level, the prolonged QT interval and an increased dispersion of repolarization times among ventricular myocytes provide the sine qua non for the initiation of TdP, a type of polymorphic VT that can lead to syncope (if transient and self-terminating) or SCD (if sustained and degenerating to VF).

Several drugs that are currently used to treat cardiovascular, neuronal, infectious diseases or other conditions are associated with increased risk of prolonging the QT interval, which is considered as a substrate for the life-threatening ventricular tachycardia, Torsade de Pointes (TdP). Therefore, drug-induced QT interval prolongation is generally used as a proxy for an increased risk of TdP, i.e. risk of SCD. Drug-induced QT-interval prolongation is most often due to a concentration-dependent inhibition of the delayed-rectifier $K^+$ current encoded by human-ether-a-go-go (hERG) gene. Examples of drugs that causes QT interval prolongation include but not limited to anti-arrhythmics, antipsychotics, anti-depressants, anti-viral agents, antibiotics, and other medications. A list of drugs that have been shown to prolong the QT interval is available at https://www.crediblemeds.org/everyone/composite-list-all-qtdrugs/.

SUMMARY 4-(Pyrimidin-2-ylmethyl)-7-(4-(trifluoromethoxy)phenyl)-3,4-dihyd robenzo[f][1,4]oxazepin-5(2H)-one (Compound 1) and 4-(pyrimidin-2-ylmethyl)-7-(4-(trifluoromethyl)phenyl)-3,4-dihydrobenzo[f][1,4]oxazepin-5(2H)-one (Compound 2) are potent and selective inhibitors of the cardiac late sodium current (INa). It has surprisingly been found that 4-(pyrimidin-2-ylmethyl)-7-(4-(trifluoromethoxy)phenyl)-3,4-dihydrobenzo[f][1,4]oxazepin-5(2H)-one is effective in treating long QT syndrome in humans, specifically LQT3. Advantageously, 4-(pyrimidin-2-ylmethyl)-7-(4-(trifluoromethoxy)phenyl)-3,4-dihydrobenzo[f][1,4]oxazepin-5(2H)-one does not show QT prolongation (does not inhibit the IKr channel) and does not inhibit cytochrome P450 (CYP) enzymes or P-glycoproteins.

Provided herein is a method for reducing the prolongation of the QT interval in a human patient, said method comprising administering to the patient an effective amount of Compound 1 or Compound 2:

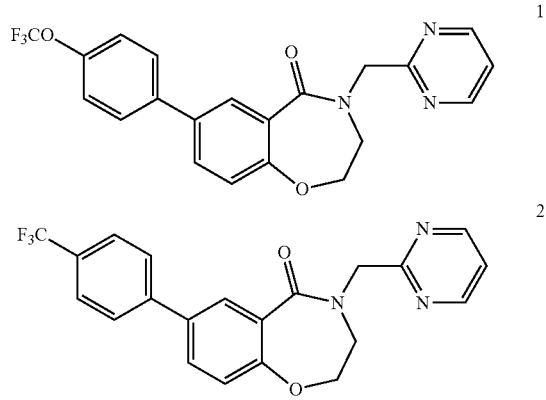

or a pharmaceutically acceptable salt thereof, wherein the prolongation of the QT interval is caused by a genetic mutation of SCN5A.

Also provided herein is a method for reducing QTc interval assessed by an echocardiogram or magnetic resonance imaging in a human patient, said method comprising administering to the patient an effective amount of Compound 1 or Compound 2:

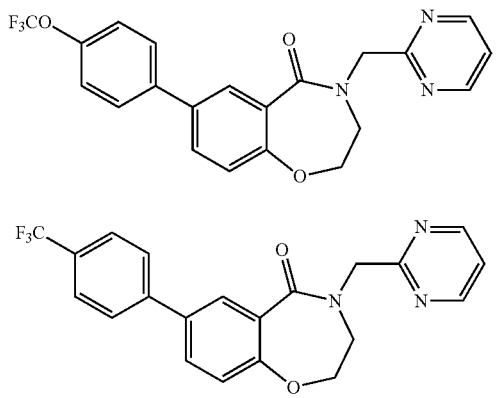

or a pharmaceutically acceptable salt thereof, wherein the QTc interval is caused by a genetic mutation of SCN5A.

Provided herein is a method for reducing the prolongation of the QT interval in a human patient, said method comprising administering to the patient an effective amount of Compound 1:

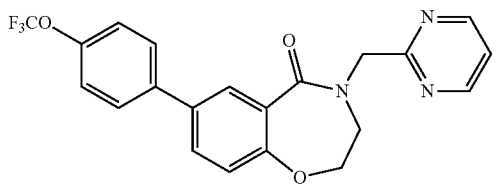

or a pharmaceutically acceptable salt thereof, wherein the prolongation of the QT interval is caused by a genetic mutation of SCN5A.

Also provided herein is a method for reducing QTc interval assessed by an echocardiogram or magnetic resonance imaging in a human patient, said method comprising administering to the patient an effective amount of Compound 1:

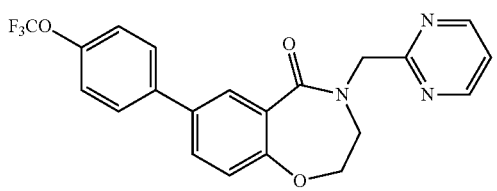

or a pharmaceutically acceptable salt thereof, wherein the QTc interval is caused by a genetic mutation of SCN5A.

Also provided herein is a method for treating LQT syndrome in a human patient, said method comprising administering to the patient an effective amount of Compound 1 or 2:

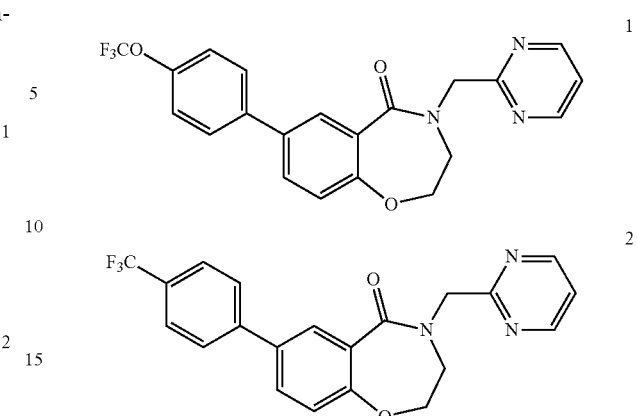

or a pharmaceutically acceptable salt thereof.

Also provided herein is a method for treating LQT3 syndrome in a human patient, said method comprising administering to the patient an effective amount of Compound 1:

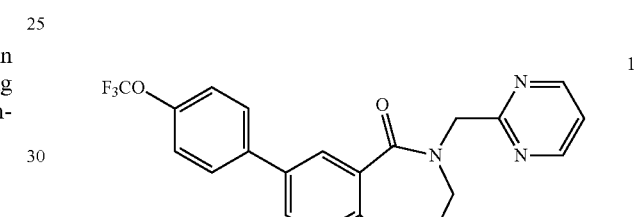

or a pharmaceutically acceptable salt thereof.

Also provided herein is a method for treating LQT1 or LQT2 syndrome in a human patient, said method comprising administering to the patient an effective amount of Compound 1:

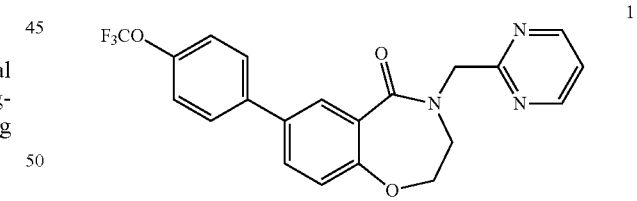

or a pharmaceutically acceptable salt thereof.

Also provided herein is a method for reducing QT prolongation comprising administering a therapeutically effective amount of 4-(pyrimidin-2-ylmethyl)-7-(4-(trifluoromethoxy)phenyl)-3,4-dihydrobenzo[f][1,4]oxazepin-5(2H)-one to a human patient in need thereof.

Also provided herein is 4-(pyrimidin-2-ylmethyl)-7-(4-(trifluoromethyl)phenyl)-3,4-dihydrobenzo[f][1,4]oxazepin-5(2H)-one (Compound 2) useful for the treatment of Long QT syndrome. Accordingly, also provided herein is a method for treating LQT1, LQT2 or LQT3 syndrome in a human patient, said method comprising administering to the patient an effective amount of a compound of formula:

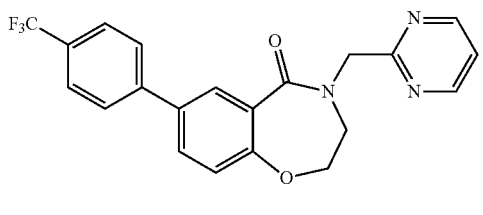

or a pharmaceutically acceptable salt thereof

Also provided is the use of Compound 1 or Compound 2:

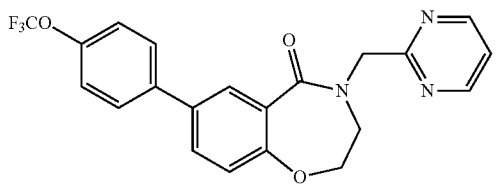

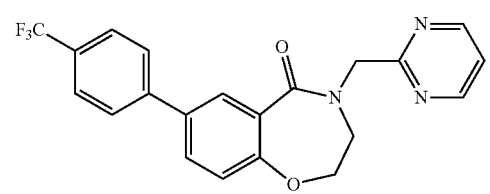

or a pharmaceutically acceptable salt thereof, for the manufacture of a medicament for treating LQT syndrome.

Also provided is the use of Compound 1 or Compound 2:

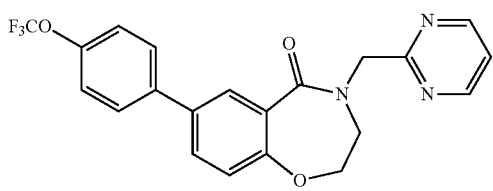

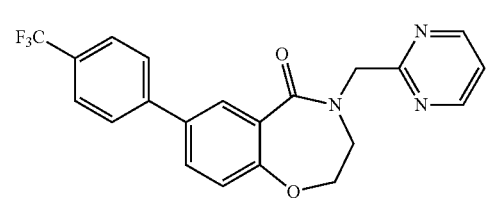

or a pharmaceutically acceptable salt thereof, for the manufacture of a medicament for reducing the prolongation of the QT interval in a human patient.

Also the use of Compound 1 or Compound 2:

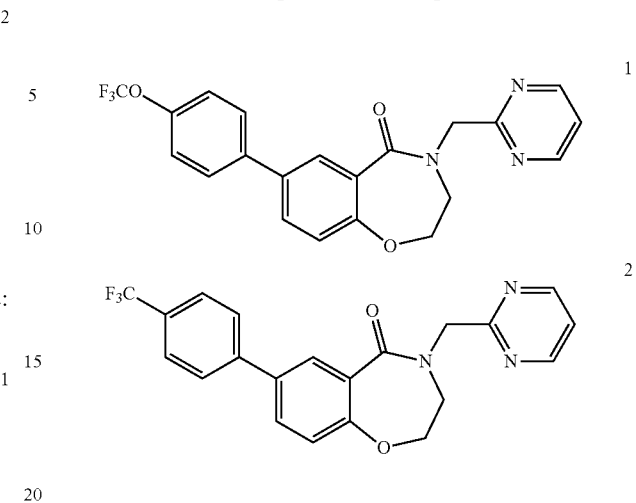

or a pharmaceutically acceptable salt thereof, for the manufacture of a medicament for use in reducing QTc interval as assessed by an echocardiogram or magnetic resonance imaging in a human patient.

BRIEF DESCRIPTION OF THE FIGURES

FIG. 5 shows mean changes in Average Daytime QTc in patients with LQT-3. The effect of Compound (I) on QTc shortening was shown to be dose-dependent with a larger QTc shortening after 40 mg on Day 2 compared to 20 mg on Day 1. The effect of QTc shortening was sustained during the maintenance doses of 6 mg from Days 3-7.

FIG. 6 shows the maximal QTc Changes on Day 2 and Day 7 compared to the predose baseline value for each in patients with LQT-3. This figure shows that the QTc shortening is sustained during the dosing period in each in patients with LQT-3.

DETAILED DESCRIPTION

1. Definitions

Figure 1:
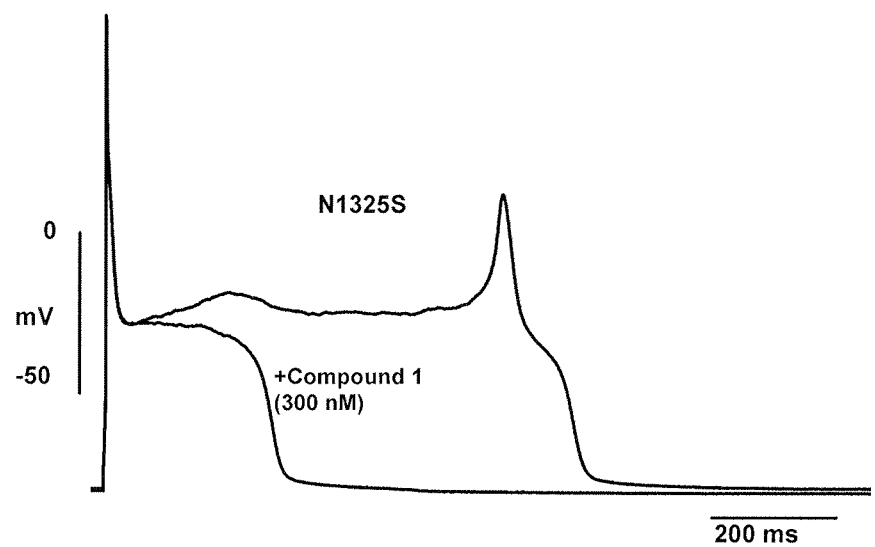
FIG. 1 shows shortening of the action potential duration (APD) in a model of LQT-3.

As used in the present specification, the following words and phrases are generally intended to have the meanings as set forth below, except to the extent that the context in which they are used indicates otherwise.

It is to be noted that as used herein and in the claims, the singular forms "a," "an" and "the" include plural referents unless the context clearly dictates otherwise. Thus, for example, reference to "a pharmaceutically acceptable carrier" in a composition includes two or more pharmaceutically acceptable carriers, and so forth.

"Comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

The term "effective amount" refers to that amount of a compound that is sufficient to effect treatment, as defined below, when administered to a mammal in need of such treatment. The effective amount will vary depending upon the specific activity of the therapeutic agent being used, the severity of the patient's disease state, and the age, physical condition, existence of other disease states, and nutritional status of the patient. Additionally, other medication the patient may be receiving will affect the determination of the effective amount of the therapeutic agent to administer.

The term "cardiac dysfunction" refers to a symptom or disease characterized by abnormalities in heart function. Non-limiting examples include, long QT syndrome, wherein there is a delayed repolarization of the heart following a heartbeat, and Torsade de Pointes, a form of irregular heartbeat that originates from the ventricles.

"Long QT Syndrome" or "LQTS" is caused by dysfunction of protein structures in the heart cells called ion channels. These channels control the flow of ions like potassium, sodium and calcium molecules. The flow of these ions in and out of the cells produces the electrical activity of the heart. Abnormalities of these channels can be acquired or inherited. The acquired form is usually caused by prescription medications, however, the inherited form occurs when a mutation develops in one of several genes that produce or "encode" one of the ion channels that control electrical repolarization. The mutant gene produces abnormal channels to be formed, and as these abnormal channels are not as efficient as the normal channels, the electrical recovery of the heart takes longer. This is manifested on the electrocardiogram (ECG, EKG) by a prolonged QT interval.

"QT prolongation", or a prolonged QT interval, makes the heart vulnerable to polymorphic ventricular tachycardias, one kind of which is a fast, abnormal heart rhythm known as Torsade de Pointes. The corrected QT interval (or "QTc") represents the QT interval corrected by heart rate. There are several methods for calculating the QTc, such as Bazett's formula ($QT_B = QT/\sqrt{RR}$), Fridericia's formula ($QT_F = QT/\sqrt[3]{RR}$), or a regression-based approach ($QT_{LC} = QT + 0.154(1-RR)$), where RR is the interval from the onset of one QRS complex to the onset of the next QRS complex.

The congenital LQTS is caused by mutations of at least one of thirteen genes:

| Clinical Name | Gene Name | Ion Channel Affected |
|---|---|---|
| LQT1 | KCNQ1 (KvLQT1) | $I_{Ks}$ |
| LQT2 | KCNH2 (hERG) | $I_{Kr}$ |
| LQT3 | SCN5A | $I_{Na}$ (late) |
| LQT4 | Ankyrin B | $I_{Na}$ (late) |
| LQT5 | KCNE1 (MinK) | $I_{Ks}$ |
| LQT6 | KCNE2 (Mirp1) | $I_{Kr}$ |
| LQT7 | KCNJ2 | $I_{K1}$ (Kir2.1) |
| LQT8 | CACNA1C | $I_{CaL}$ |
| LQT9 | CAV3 | $I_{Na}$ (late) |
| LQT10 | SCN4B | $I_{Na}$ (late) |
| LQT11 | AKAP9 | $I_{Ks}$ |
| LQT12 | SNTA1 | $I_{Na}$ (late) |
| LQT13 | GIRK1 (KCNJ5) | $I_{KACh}$ |

*Homozygous carriers of novel mutations of KvLQT1 have Jervell, Lange-Nielsen syndrome. KvLQT1 and MinK coassemble to form the $I_{Ks}$ channel.

The inherited form of LQTS occurs when a mutation develops in one of several genes that produce or "encode" one of the ion channels that control electrical repolarization. There are at least thirteen different forms of inherited LQTS, characterized as LQT1 through LQT13. They were originally characterized by the differing shape of the EKG trace, and have subsequently been associated with specific gene mutations. The LQT1 form is the most frequent, accounting for approximately 40-45% of the genotyped patients. LQT2 is next at about 35-40%, and LQT3, from SCN5A mutations accounts for about 5-10%. Patients with two mutations seem to account for less than 1% of all patients, but this may change as more patients are studied with the newer genetic techniques.

The term "treatment" or "treating" means any administration of a compound according to the present disclosure to a subject (e.g. human) having or susceptible to a condition or disease disclosed herein for the purpose of: 1) preventing or protecting against the disease or condition, that is, causing the clinical symptoms not to develop; 2) inhibiting the disease or condition, that is, arresting or suppressing the development of clinical symptoms; or 3) relieving the disease or condition that is causing the regression of clinical symptoms. In some embodiments, the term "treatment" or "treating" refers to relieving the disease or condition, i.e. which is causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment. The presence of a genetic mutation or the predisposition to having a mutation may not be alterable. However, prophylactic treatment (prevention) as used herein has the potential to avoid/ameliorate the symptoms or clinical consequences of having the disease engendered by such genetic mutation or predisposition.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

As used herein the phrase "reducing QTc interval" is synonymous with the phrase "shortening QTc."

sho iThe teem "patient" typically refers to a "mammal" which includes, without limitation, human, monkeys, rabbits, mice, domestic animals, such as dogs and cats, farm animals, such as cows, horses, or pigs, and laboratory animals. In some embodiments, the term patient refers to a human in need of treatment as defined herein.

"Administering" or "administration" refers to the delivery of one or more therapeutic agents to a patient. In one embodiment, the administration is coadministration such that two or more therapeutic agents are delivered together at one time. In certain embodiments, two or more therapeutic agents can be coformulated into a single dosage form or "combined dosage unit", or formulated separately and subsequently combined into a combined dosage unit, typically for intravenous administration or oral administration.

"Intravenous administration" is the administration of substances directly into a vein, or "intravenously". Compared with other routes of administration, the intravenous (IV) route is the fastest way to deliver fluids and medications throughout the body. An infusion pump can allow precise control over the flow rate and total amount delivered, but in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used, which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, a "flush", following the injection to push the medicine into the bloodstream more quickly.

"Oral administration" is a route of administration where a substance is taken through the mouth, and includes buccal, sublabial and sublingual administration, as well as enteral administration and that through the respiratory tract, unless made through e.g. tubing so the medication is not in direct contact with any of the oral mucosa. Typical form for the oral administration of therapeutic agents includes the use of tablets or capsules.

A "sustained release formulation" is a formulation which is designed to slowly release a therapeutic agent in the body over an extended period of time, whereas an "immediate release formulation" is a formulation which is designed to quickly release a therapeutic agent in the body over a shortened period of time. In some cases the immediate release, formulation may be coated such that the therapeutic agent is only released once it reached the desired target in the body (e.g. the stomach).

The term "compound" is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H, $^{13}$C, and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have two of the three substituents on nitrogen ($R^{30}$, $R^{31}$, and $R^{32}$) as hydrogen, disubstituted amines have one of the three substituents on nitrogen ($R^{30}$, $R^{31}$, and $R^{32}$) as hydrogen, whereas trisubstituted amines have none of the three substituents on nitrogen ($R^{30}$, $R^{31}$, and $R^{32}$) as hydrogen. $R^{30}$, $R^{31}$, and $R^{32}$ are selected from a variety of substituents such as hydrogen, optionally substituted alkyl, aryl, heteroaryl, cycloalkyl, cycloalkenyl, heterocyclyl, and the like. The above-mentioned amines refer to the compounds wherein one, two, or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein, and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, or unless otherwise indicated herein, its use in the therapeutic compositions is contemplated. Supplementary active ingredients can also be incorporated into the compositions.

2. Methods

Generally, the present disclosure relates to methods for reducing the prolongation of the QT interval in a human patient, said method comprising administering to the patient an effective amount of Compound 1 or Compound 2:

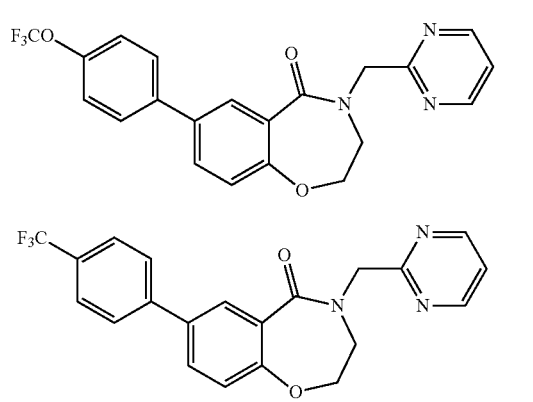

or a pharmaceutically acceptable salt thereof, wherein the prolongation of the QT interval is caused by a genetic mutation of SCN5A.

In another embodiment, the present disclosure provides a method for reducing the prolongation of the QT interval in a human patient, said method comprising administering to the patient an effective amount of Compound 1:

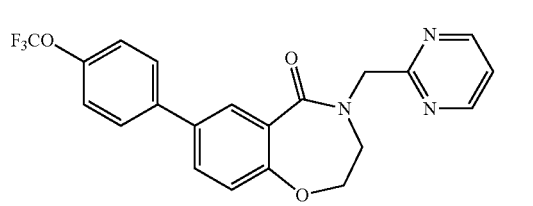

or a pharmaceutically acceptable salt thereof, wherein the prolongation of the QT interval is caused by a genetic mutation of SCN5A.

In another embodiment, the present disclosure provides a method for shortening QTc in a patient in need thereof, comprising administering to the patient an effective amount of Compound 1 or Compound 2:

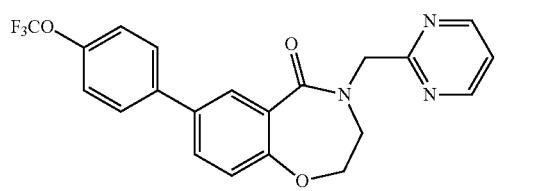

-continued

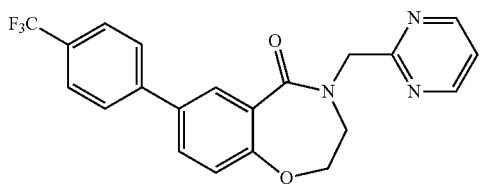

or a pharmaceutically acceptable salt thereof.

In another embodiment, the present disclosure provides a method for reducing QTc interval assessed by an echocardiogram or magnetic resonance imaging in a human patient, said method comprising administering to the patient an effective amount of Compound 1 or Compound 2:

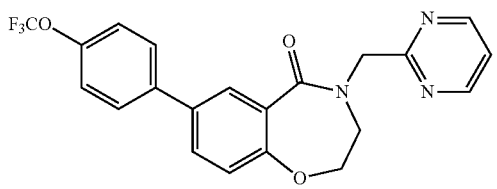

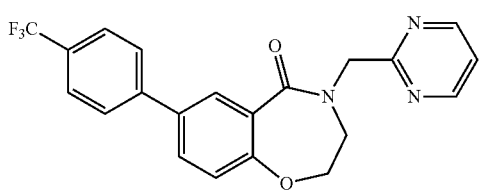

or a pharmaceutically acceptable salt thereof, wherein the QTc interval is caused by a genetic mutation of SCN5A.

In one embodiment, the present disclosure provides methods for reducing QTc interval as assessed by an echocardiogram or magnetic resonance imaging in a human patient, said method comprising administering to the patient an effective amount of Compound 1:

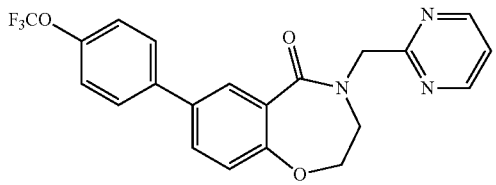

or a pharmaceutically acceptable salt thereof, wherein the QTc interval is caused by a genetic mutation of SCN5A.

In one embodiment, the present disclosure provides methods for treating cardiac dysfunction in a human patient, said method comprising administering to the patient an effective amount of Compound 1:

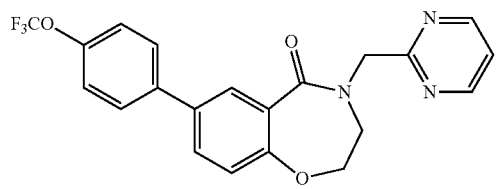

or a pharmaceutically acceptable salt thereof, wherein the cardiac dysfunction is caused by a genetic mutation of SCN5A.

In one embodiment, the cardiac dysfunction is assessed by an echocardiogram or magnetic resonance imaging.

In one embodiment, the present disclosure provides a method for treating LQT syndrome in a human patient, said method comprising administering to the patient an effective amount of Compound 1 or 2:

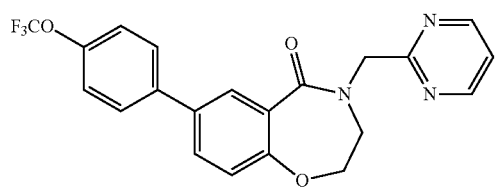

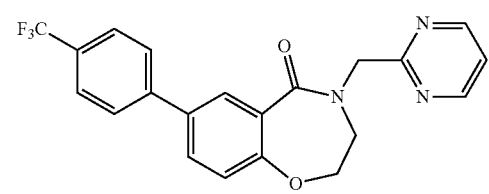

or a pharmaceutically acceptable salt thereof.

In another embodiment the present disclosure provides for the treatment or prevention of LQT3 syndrome in a human patient, said method comprising administering to the patient an effective amount of Compound 1 or 2:

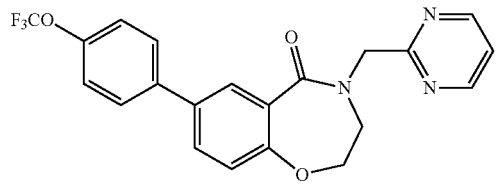

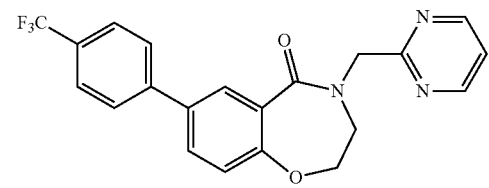

or a pharmaceutically acceptable salt thereof.

In another embodiment, the present disclosure provides a method for treating LQT3 syndrome in a human patient, said method comprising administering to the patient an effective amount of Compound 1:

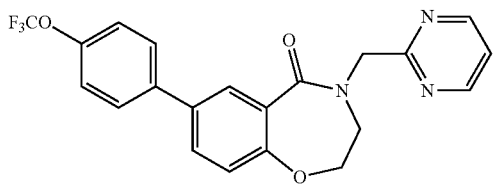

or a pharmaceutically acceptable salt thereof.

In one embodiment, the present disclosure relates to a method of treating (reducing) drug induced QT prolongation in a human patient comprising administering a therapeutically effective amount of compound 1 or compound 2 or a pharmaceutically acceptable salt thereof. For example, QT prolongation resulting from administration of dofetilide, methadone, erythromycin, cisapride, moxifloxacin, or ziprasidone may be reduced by administration of compound 1 or compound 2.

In one embodiment, the disclosure is directed to a method of preventing arrhythmias in mammals afflicted with LQT3 comprising administering' an effective amount of Compound 1:

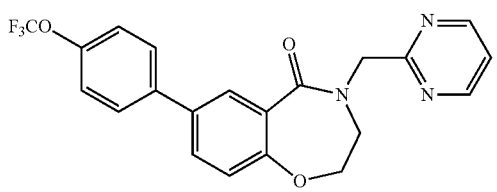

or a pharmaceutically acceptable salt thereof.

In yet another embodiment, the disclosure is directed to a method of treating or preventing arrhythmias in a mammal afflicted with LQT1, LQT2 or LQT3 syndrome comprising administering an effective amount of Compound 1:

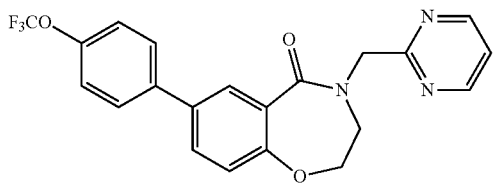

or a pharmaceutically acceptable salt thereof.

3. Compounds

Embodiments of the present disclosure comprise Compound 1:

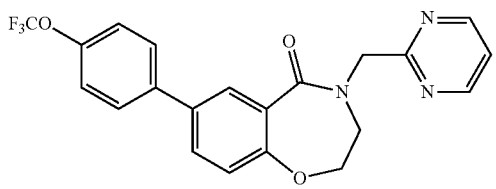

which is named 4-(pyrimidin-2-ylmethyl)-7-(4-(trifluoromethoxy)phenyl)-3,4-dihydrobenzo[f][1,4]oxazepin-5(2H)-one, or a pharmaceutically acceptable salt thereof.

Other embodiments of the present disclosure comprise Compound 2:

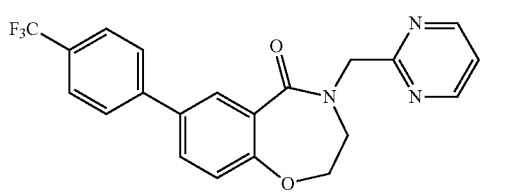

which is named 4-(pyrimidin-2-ylmethyl)-7-(4-(trifluoromethoxy)phenyl)-3,4-dihydrobenzo[f][1,4]oxazepin-5(2H)-one, or a pharmaceutically acceptable salt thereof.

Compounds 1 and 2 can be prepared according to Example 1 below, and are described in US 2013/0012492, which is hereby incorporated by reference in its entirety for all purposes. Compounds 1 and 2 are potent late sodium channel inhibitors (see, US patent publication 2013/0012492).

4. Administration

Compound 1 or 2 may be given to the patient in either single or multiple doses by any of the accepted modes of administration of agents having similar utilities, for example as described in those patents and patent applications incorporated by reference. Modes of administration includes buccal, intra-arterial injection, intravenously, intraperitoneally, parenterally, intramuscularly, subcutaneously, orally, or via an impregnated or a coated device such as a stent, for example, or an artery-inserted cylindrical polymer. In one embodiment, Compound 1 is administered intravenously. In one embodiment, Compound 2 is administered intravenously.

In one embodiment, Compound 1 is administered orally, such as, for example, in a tablet. In one embodiment, Compound 1 is administered to a human patient in need thereof in an effective amount, such as, from about 1 mg to about 1 g per day. In one embodiment, the effective amount is from about 0.1 mg to about 200 mg per day. In one embodiment, the effective amount is from about 1 mg to about 100 mg per day. In other embodiments, the effective amount is about 1 mg, about 3 mg, about 6 mg, about 9 mg, about 10 mg, about 12 mg, about 18 mg, about 20 mg, about 30 mg, about 40 mg, about 60 mg, about 80 mg, or about 100 mg per day. In other embodiments, the effective amount is about 1 mg, 3 mg, 6 mg, 9 mg, 12 mg or 18 mg per day. In certain embodiments, Compound 1 is administered once a day. In yet another embodiment, Compound I is administered as a loading dose of from about 10 mg to about 60 mg on the first day (and optionally on days 2, 3 and/or 4) of treatment followed by a maintenance dose of 1 mg, 2 mg, 3 mg, 5 mg, 6 mg or 10 mg daily thereafter. In another embodiment, the qualified caregiver is able to tailor a dose regimen to fit with the particular needs of the patient. Thus, it will be understood that the amount of the compound actually administered usually will be determined by a physician, in light of the relevant circumstances, including the condition(s) to be treated, the chosen route of administration, the actual compound (e.g. salt or free base) administered and its relative activity, the age, weight, and response of the individual patient, the severity of the patient's symptoms, and the like.

In one embodiment, Compound 2 is administered orally, such as, for example, in a tablet. In one embodiment, Compound 2 is administered to a human patient in need thereof in an effective amount, such as, e.g., from about 1 mg to about 1 g per day. In one embodiment, the effective amount is from about 0.1 mg to about 200 mg per day. In one embodiment, the effective amount is from about 1 mg to about 100 mg per day. In other embodiments, the effective amount is about 1 mg, about 3 mg, about 6 mg, about 9 mg, about 10 mg, about 12 mg, about 18 mg, about 20 mg, about 30 mg, about 40 mg, about 60 mg, about 80 mg, or about 100 mg per day. In other embodiments, the effective amount is about 1 mg, 3 mg, 6 mg, 9 mg, 12 mg or 18 mg per day. In certain embodiments, Compound 2 is administered once a day. In yet another embodiment, Compound 2 is administered as a loading dose of from about 10 mg to about 60 mg on the first day (and optionally on days 2, 3 and/or 4) of treatment followed by a maintenance dose of 1 mg, 2 mg, 3 mg, 5 mg, 6 mg or 10 mg daily thereafter. In another embodiment, the qualified caregiver is able to tailor a dose regimen to fit with the particular needs of the patient. Thus, it will be understood, however, that the amount of the compound actually administered usually will be determined by a physician, in the light of the relevant circumstances, including the condition(s) to be treated, the chosen route of administration, the actual compound (e.g. salt or free base) administered and its relative activity, the age, weight, and response of the individual patient, the severity of the patient's symptoms, and the like.

5. Pharmaceutical Formulations

Compound 1 or 2 may be administered in a pharmaceutical formulation. Formulations contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include Compound 1 or 2, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure can be formulated so as to provide quick, sustained or delayed release of the active ingredient after administration to the patient by employing procedures known in the art. In certain embodiments, sustained release formulations are used. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345.

The compositions are preferably formulated in a unit dosage form. The term "unit dosage forms" or "combined dosage unit" refers to physically discrete units suitable as unitary dosages for human subjects and other mammals, each unit containing a predetermined quantity of the active materials calculated to produce the desired effect, in association with a suitable pharmaceutical excipient (e.g., a tablet, capsule, ampoule). The active agents of the disclosure are effective over a wide dosage range and are generally administered in an effective amount. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredients are mixed with a pharmaceutical excipient to form a solid preformulation composition containing a homogeneous mixture of a compound of the present disclosure. When referring to these preformulation compositions as homogeneous, it is meant that the active ingredients are dispersed evenly throughout the composition so that the composition may be readily subdivided into equally effective unit dosage forms such as tablets, pills and capsules.

The tablets or pills comprising Compound (I) of the present disclosure may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. Compound 1 or 2 and the co-administered agent(s) may be separated by an enteric layer that serves to resist disintegration in the stomach and permit the inner element to pass intact into the duodenum or to be delayed in release. A variety of materials may be used for such enteric layers or coatings, such materials including a number of polymeric acids and mixtures of polymeric acids with such materials as shellac, cetyl alcohol, and cellulose acetate.

Activity testing is conducted in the Examples below using methods described herein and those well known in the art.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure. Throughout, abbreviations used have the following meanings.

| Abbreviation | Meaning |
| --- | --- |
| ° C. | Degree Celsius |
| ACN | Acetonitrile |
| ADME | Absorption, Distribution, Metabolism and Excretion |
| AP | Action Potential |
| APD | Action Potential Duration |
| ATX II | Anemonia sulcata toxin |
| cm | Centimeter |
| $C_{max}$ | Maximum Concentration |
| conc | Concentrated |
| CYP | Cytochrome Enzyme |
| d | Doublet |
| DCM | Dichloromethane |
| dd | Doublet of doublets |
| DMF | Dimethylformamide |
| DMSO/dmso | Dimethylsulfoxide |
| dppf | 1,1'-Bis(diphenylphosphino)ferrocene |
| EAD | Early afterdepolarization |
| ECG/EKG | Electrocardiogram |
| ECHO | Echocardiogram |
| eq | Equivalents |
| Et | Ethyl |
| g | Grams |
| h | Hours |
| hERG | human Ether-à-go-go Related Gene |
| HPLC | High-performance liquid chromatography |
| Hz | Hertz |
| IKr | Cardiac rapid delayed rectifier current |
| INa | Cardiac late sodium current |
| i.m. | Intramuscular |
| i.v. | Intravenous |
| iPr | iso-Propyl |
| J | Coupling constant |
| Kg | Kilogram |
| LC | Liquid chromatography |
| LQT/LQTS | Long QT Syndrome |
| M | Molar |
| m | multiplet |
| m/z | mass-to-charge ratio |
| M+ | Mass peak |
| M + H | Mass peak plus hydrogen |
| $MAPD_{90}$ | Monophasic action potential duration at 90% repolarization |
| mg | Milligram |
| MHz | Megahertz |
| min/m | Minute |
| ml/mL | Milliliter |
| mM | Millimolar |
| mm | Millimeter |
| mmol | Millimole |
| Mol | Mole |
| MRI | Magnetic Resonance Imaging |
| MS | Mass spectroscopy |
| ms | Millisecond |

-continued

| Abbreviation | Meaning |
| --- | --- |
| mV | Millivolt |
| N | Normal |
| nM | Nanomolar |
| NMR | Nuclear magnetic resonance |
| PK | Pharmacokinetics |
| prep | Preparative |
| QT | QT interval |
| QTc | Corrected QT interval |
| RT/rt | Room temperature |
| s | Second |
| s | Singlet |
| t | Triplet |
| THF | Tetrahydrofuran |
| δ | Chemical shift |
| µA | Microamps |
| µg | Microgram |
| µL/µl | Microliter |
| µM | Micromolar |
| VT | Ventricular tachycardia |

Example 1

4-(pyrimidin-2-ylmethyl)-7-(4-(trifluoromethoxy)phenyl)-3,4-dihydrobenzo[f][1,4]oxazepin-5(2H)-one (Compound 1)

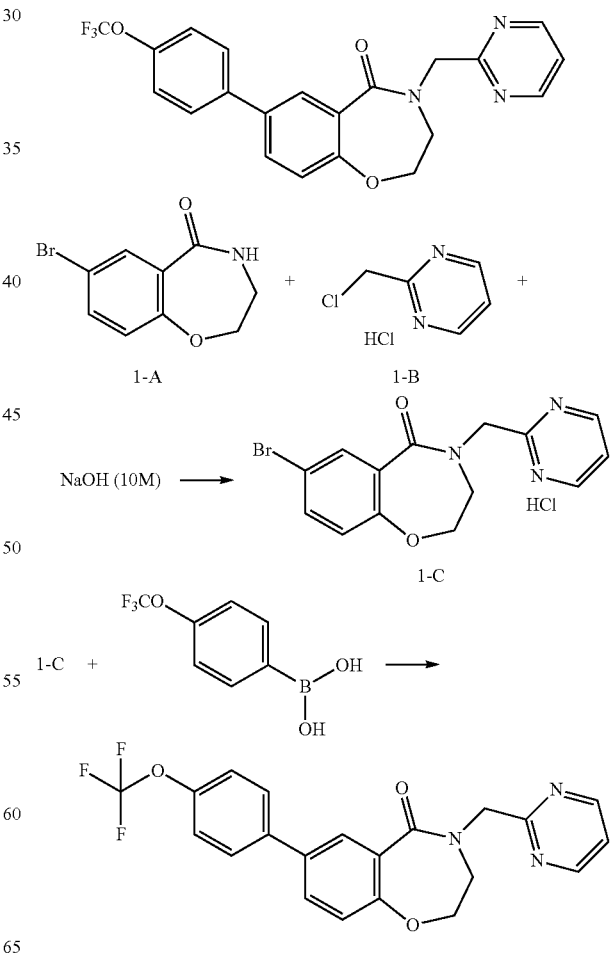

-continued

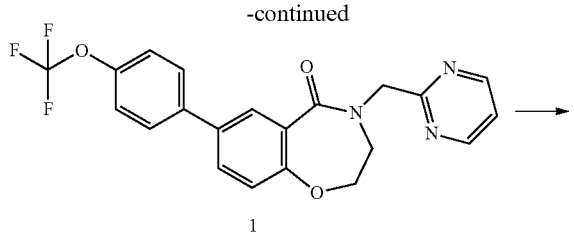

1

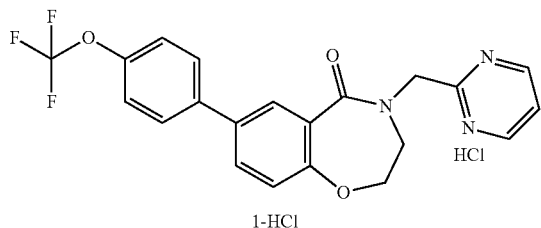

1-HCl

To a solution of Compound 1-A (20 g, 0.083 mol, 1 eq.) and Compound 1-B (25 g, 0.15 mol, 1.8 eq.) in DMF (150 mL), NaOH solution (20 mL, 10 M, 5 eq.) was slowly added at room temperature (slightly exothermic) and stirred at r.t. for 10 min, followed by heating at 95° C. for 2 h. After cooling the reaction mixture, ethyl acetate (200 mL) was added and the organic layer was separated. The organics was washed with water (20 mL), brine, dried over sodium sulphate and concentrated.

The residue was dissolved in 1,4-dioxane (50 mL) and to this 4 N HCl in dioxane (50 mL) and conc. HCl (2 mL) was added and stirred at room temperature for 4 h, filtered the precipitate, washed with ethyl acetate and dried. Compound 1-C was obtained (30 g) as a light yellow solid.

To the bromide (15 g, 0.04 mol, 1 eq), boronic acid (12.5 g, 0.06 mol, 1.5 eq) and potassium carbonate (22 g, 0.16 mol, 4 eq) in a round bottom flask, solvent (150 mL, toluene/isopropanol/water: 2/1/1) was added and stirred under nitrogen for 10 min. To the above solution the palladium catalyst (1 g, 0.012 mol, 0.02 eq) was added and heated at 85° C. for 2 h. The reaction mixture was diluted with ethyl acetate, separated the organic layer and filtered the organic layer through a plug of celite and silica gel and concentrated. Column purification on silica gel using ethyl acetate/hexane as eluent provided Compound 1 (13 g).

To a solution of Compound 1 (26 g) in 1,4-dioxane (25 mL), 4N HCl/dioxane (25 mL) was added followed by conc. HCl (2 mL) and stirred at room temperature for 4 h. Solvent was distilled off, dichloromethane was added and distilled off and to the residue, ethyl acetate (150 mL) was added and stirred at room temperature overnight and filtered the precipitate, washed with ethyl acetate, hexane and dried under vacuum. Compound 1-HCl obtained (24.8 g) was a white solid.

$^1$H-NMR (CDC$_3$) δ 8.72 (d, 2H, J=5.2 Hz), 8.17 (d, 1H, J=2.4 Hz), 7.59-7.63 (m, 3H), 7.26 (d, 2H, J=3.2 Hz), 7.22 (t, 1H, J=4.8 Hz), 7.10 (d, 1H, J=8.4 Hz), 5.10 (s, 2H), 4.56 (t, 2H, J=5.0 Hz), 3.77 (t, 2H, J=5.0 Hz); MS m/z 416.1 (M+H).

Example 2

4-(pyrimidin-2-ylmethyl)-7-(4-(trifluoromethyl)phenyl)-3,4-dihydrobenzo[f][1,4]oxazepin-5(2H)-one (Compound 2)

Compound 2 is prepared in a manner similar to that of Compound 1 except that 4 trifluoromethyl phenyl boronic acid is used in place of 4-trifluoromethoxy phenyl boronic acid.

Example 3

Biological Data

Methods for testing compounds for efficacy in reducing the QT interval are known in the art.

Compound 1 exhibits shortening of the action potential duration (APD) (FIG. 1).

Figure 2:
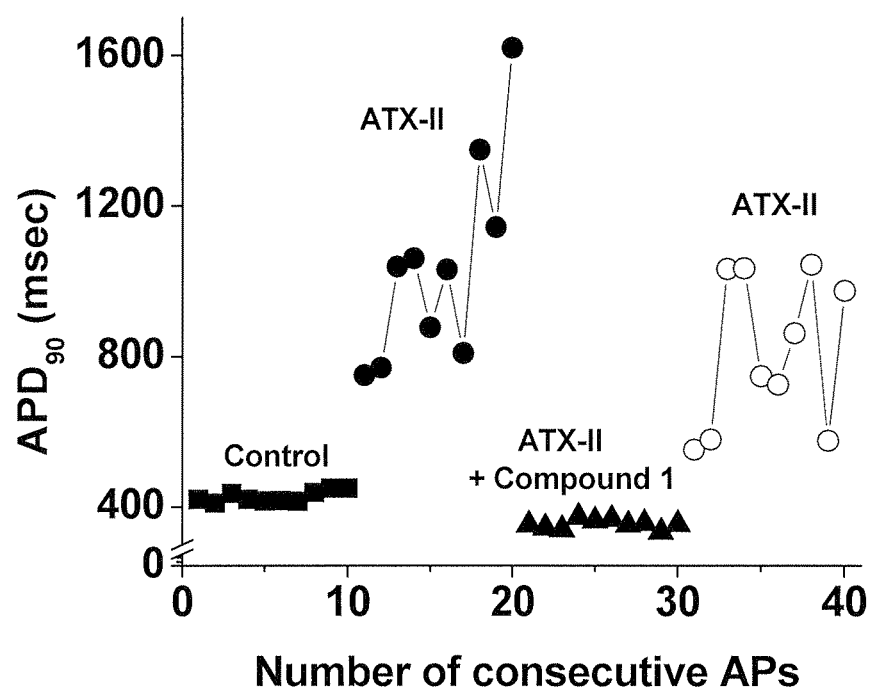
FIG. 2 shows reduction of beat-to-beat variability in a model of LQT3.

Compound 1 exhibits reduction of beat-to-beat variability in a model of long QT syndrome-3 (LQT3) (FIG. 2).

Figure 3:
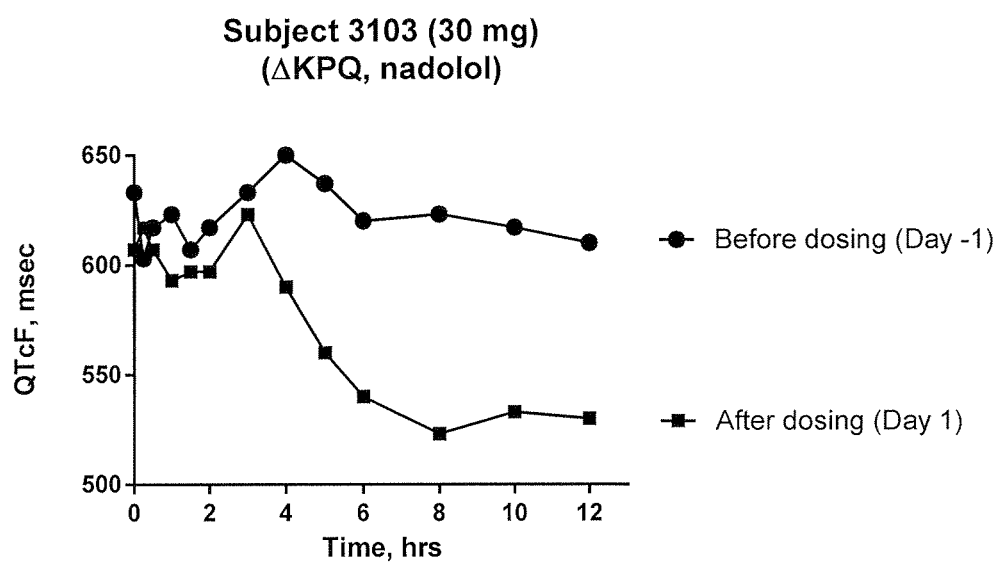
FIG. 3 shows shortening of QTc from pre-dose baseline on Day −1 in patients with LQT-3

Compound 1 exhibits changes in QTc from baseline (FIG. 3).

Figure 4:
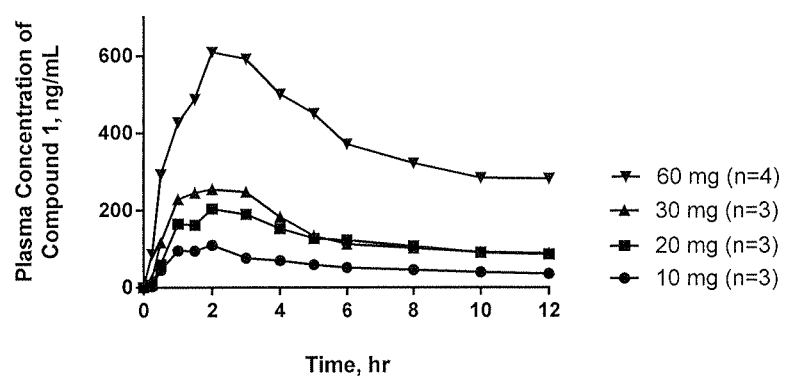
FIG. 4 shows that the PK profile of Compound 1 after single oral dose in in patients with LQT-3. This is similar to the PK profile of Compound 1 in healthy volunteers.

Compound 1 exhibits that the PK profile in LQT3 patients is similar to that in healthy volunteers (FIG. 4).

TABLE A

Potency of Ranolazine and Compound 1 on inhibition of the enhanced late $I_{Na}$ in LQT3 mutations

|  | ΔKPQ | R1623Q | N1325S | E1784K | S1787N |
|---|---|---|---|---|---|
| Ranolazine | 15 μM | 7.2 μM | 4.4 μM | ~10 μM | ~10 μM |
| Compound 1 | 0.48 μM | 0.373 μM (19-fold) | 0.518 μM (18.5 fold) | 0.404 μM (~25 fold) | 0.324 μM (~31 fold) |

At 10 mg, Compound 1 showed preliminary efficacy (QTc shortening or T-wave morphology) in three patients with inherited LQT3. After single dose administration, Compound 1 has fast absorption, a biphasic decline, low clearance and a long half-life.

In a LQT-3 clinical study, ten patients were dosed with a single dose of Compound 1 (10 mg, 20 mg, 30 mg or 60 mg). QTc was shortened in the range of 20-100 milliseconds in these subjects. Compound 1 was found to be well tolerated in the patients.

Example 4

Effect of Compound (I) in Patients with LQT3

In an ongoing Phase 1, effect of oral Compound (I) on the QTc interval in subjects with LQT3 was evaluated. Subjects with LQT3 identified from the LQTS registry with proven mutations in the cardiac sodium channel and a QTc >460 msec will be enrolled. Four sequential single dose cohorts and 1 multiple dose cohort were enrolled and received a single dose of Compound (I) (Cohort 1: 10 mg; Cohort 2: 20 mg; Cohort 3: 30 mg; Cohort-4: 60 mg) or multiple doses of Compound (I) (Cohort 5: Day 1—20 mg, Day 2—40 mg, Days 3-7—6 mg once daily).

Figure 5:
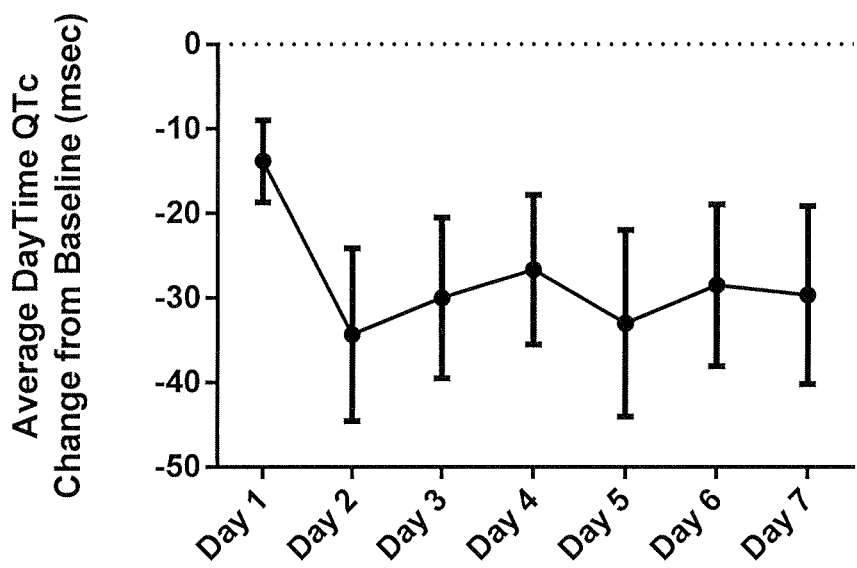
FIGS. 5 and 6 show the QTc shortening in in patients with LQT-3 who received Compound for 7 days (20 mg on Day 1, 40 mg on Day 2 and 6 mg daily on Days 3-7).
Figure 6:
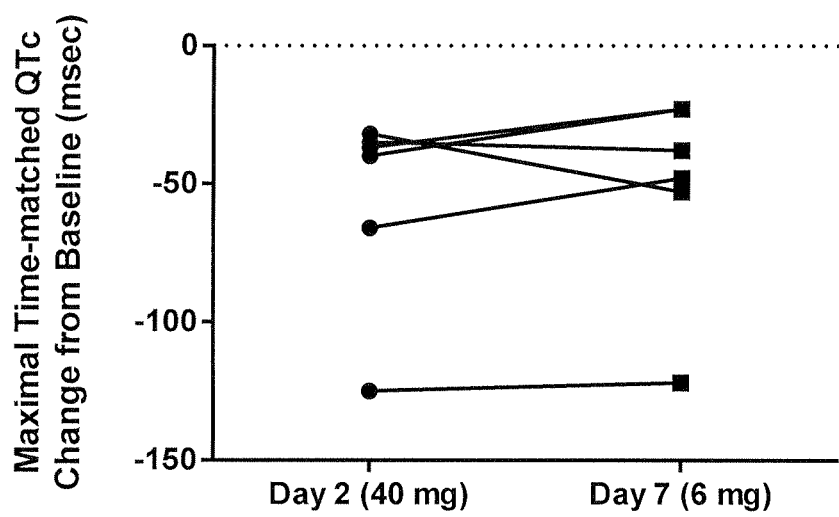

Ten subjects were enrolled. Among these 10 subjects, 3 subjects received single oral dose of Compound (I), 5 subjects received Compound (I) at 2 different dose periods, and 2 subjects received Compound (I) at 3 different dose periods. Preliminary safety assessment indicates that Compound (I) was well tolerated by all subjects. Changes in QTc interval from baseline (Day −1 for Cohorts 1-4; average of Day −2 and Day −1 for Cohort 5) were analyzed in 2 different ways: 1) changes in average daytime QTc during 12 hours postdose (QTc interval $AUC_{0-12}/12$) and 2) maximal time-matched QTc changes within 12 hours postdose. Shortening of QTc was observed at all dose levels. In the multiple dose cohort (shown in FIG. 5-6), the effect of Compound (I) on QTc shortening was dose-dependent with a larger QTc shortening after 40 mg on Day 2 compared to 20 mg on Day 1. More importantly, the QTc shortening was sustained during the maintenance doses of 6 mg from Days 3-7.

In addition, effect of Compound (I) on cardiac function was assessed by ECHO. For the single dose cohorts, echocardiography (ECHO) was performed at baseline (Day −1) and at 3 and 6 hours after the single oral dose of Compound (I) on Day 1. For the multiple dose cohort (Cohort 5), ECHO was performed at baseline (Day −1), at 3 and 6 hours after the single oral dose of Compound (I) on Day 1, and at 3 hours after dose on Day 4 and Day 7. Compound (I) did not affect the left ventricular (LV) functions assessed by ECHO.

In conclusion, based on the preliminary data for the subjects who participated in the Phase 1 studies conducted to date, Compound (I) was well-tolerated and had no effect on cardiac function measured by ECHO. Compound (I) shortens QTc interval after a single dose, which is sustained following multiple dose administration. Effect of Compound (I) on QTc shortening appears to be independent of mutations or the concomitant use of b-blockers.

Example 5

Rabbit Isolated Heart Experiments

Figure 7:
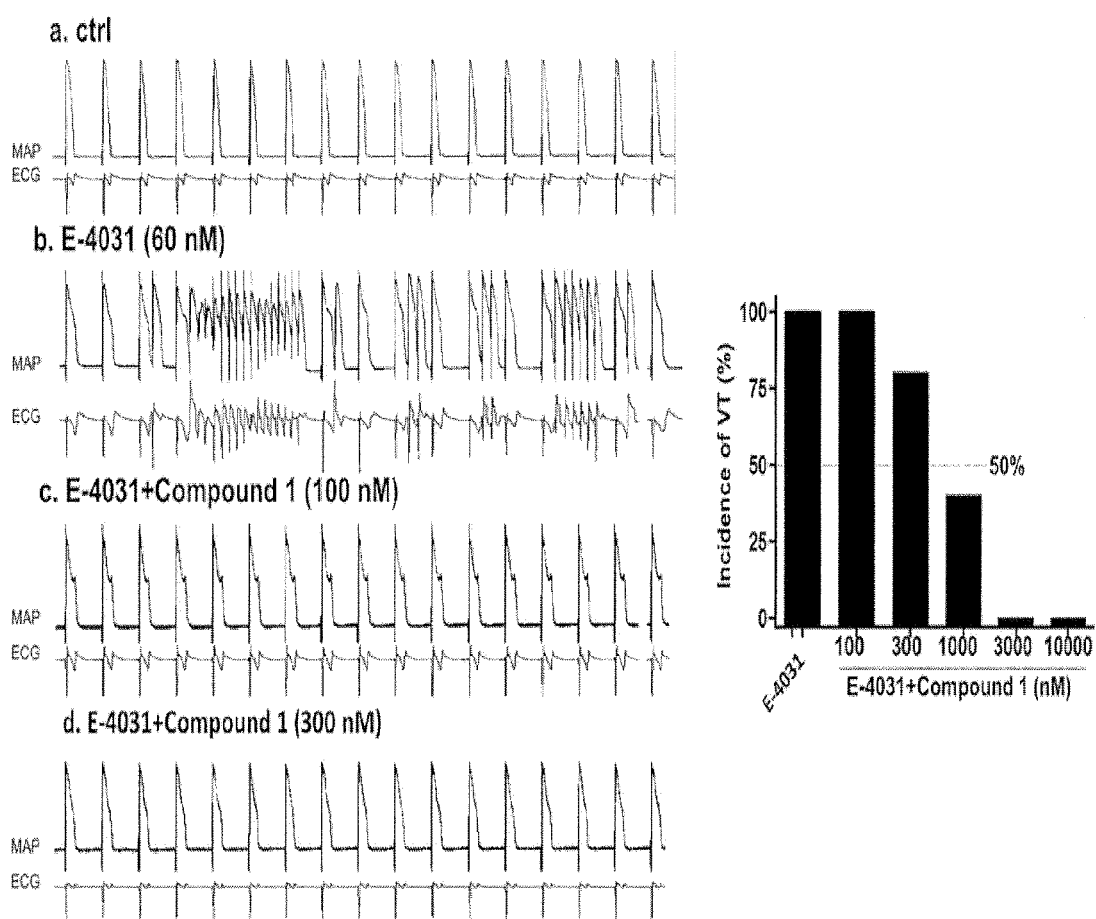
FIG. 7 shows the effects of Compound 1 in a model of LQT-2 and drug-induced QT prolongation. E-4031 is an inhibitor of IKr. Compound 1 shortens the prolonged monophasic action potential (MAP) and suppresses torsades de pointes (TdP) ventricular tachyarrhythmia induced by 60 nM E-4031 in the rabbit isolated heart. Representative sequential recordings of the left ventricular epicardial MAP (top record in each panel) and the pseudo-electrocardiogram (bottom record in each panel) during exposure of a heart to perfusate alone (ctrl, a), E-4031 (b), and 100 (c) and 300 (d) nM of Compound 1 in the continued presence of E-4031. Hearts were paced at a rate of 1 Hz. Bar graph shows the concentration-response relations for Compound 1 to reduce the incidence of TdP during exposure of hearts to E-4031.

The use of rabbits (New Zealand White adult females, 2-4 kg; Western Oregon Rabbit Company, Philomath, Oreg.) in this investigation conformed to the "*Guide for the Care and Use of Laboratory Animals*" (NIH publication No. 85-23, revised 1996) and was approved by the Institutional Animal Care and Use Committees of Gilead Sciences. Hearts were isolated and perfused by the method of Langendorff as previously described (Wu et al., 2009). Briefly, the atrioventricular nodal area was thermally ablated to produce heart block, and hearts were paced at a rate of 1 Hz. Monophasic action potentials (MAPs) from the left ventricular epicardium and pseudo 12-lead electrocardiograms (ECGs) were recorded. Following a 10-20 min period of equilibration, hearts were exposed to vehicle (modified Krebs-Henseleit buffer), E-4031, and then to increasing concentrations of Compound 1 in the continuous presence of E-4031 until a steady-state effect was reached. The duration of the MAP at the level at which repolarization is 90% complete ($MAPD_{90}$) was measured. The results are shown in FIG. 7.

Example 6

Rabbit Isolated Left Ventricular Wedge Preparations

Figure 8:
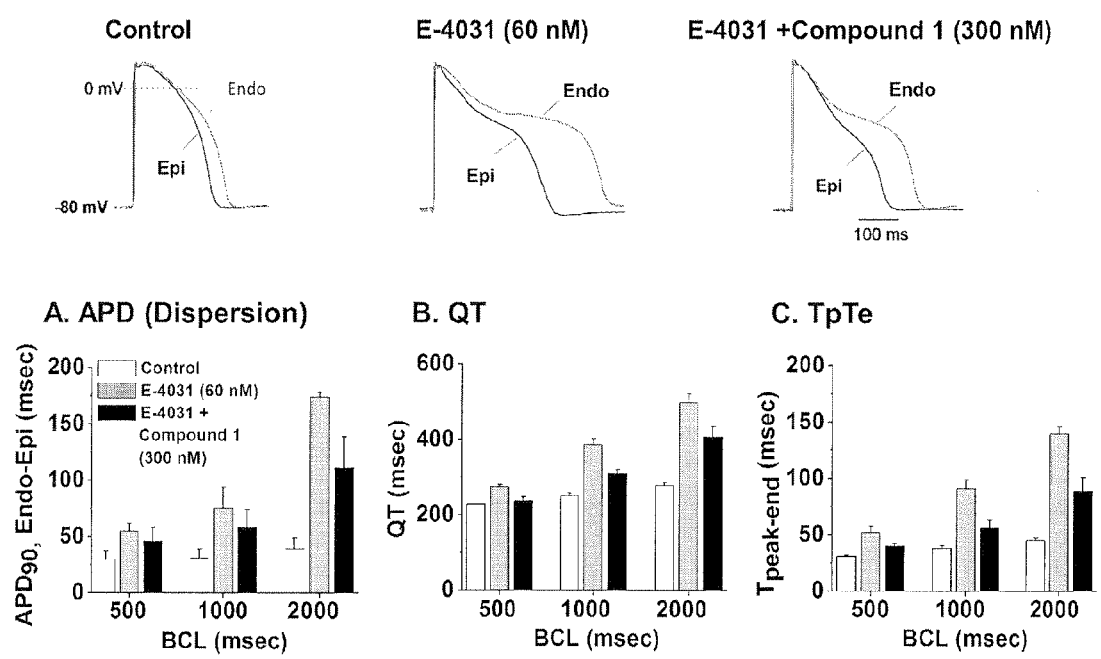
FIG. 8 shows the effects of Compound 1 in a different model of LQT-2 and drug-induced QT prolongation. E-4031 is an inhibitor of IKr. Compound 1 shortens the prolonged action potential duration (APD), QT interval and Tpeak to Tend (TpTe) that is prolonged by 60 nM E-4031 in the rabbit isolated wedge preparation. Representative original tracings of left ventricular epicardial (Epi) and endocardial (Endo) AP during exposure of a heart to perfusate alone (control), E-4031 (60 nM), and 300 nM of Compound 1 in the continued presence of E-4031. Bar graphs show the effect of Compound 1 (black bar) on APD (panel A), QT interval (panel B) and TpTe (panel C) in the continuous presence of E-4031 (gray bar) at three different cycle lengths (500, 1000 and 2000 msec, respectively).

Rabbit isolated left ventricular wedge was prepared as previously described (Yan et al, 1996, 2009). Briefly, the chest was opened via a left thoracotomy, and the heart was excised, placed in a cardioplegic solution consisting of cold (4° C.) Tyrode's solution containing 20 mmol/L $[K^-]_o$, and transported to a dissection tray. Transmural wedges with dimensions of approximately 1×1×0.8 or 0.8×0.8×0.4 cm³ were dissected from the left ventricle. The tissue was cannulated via a small (diameter, ≈100 µm) branch of the left anterior descending artery or another coronary artery and perfused with cardioplegic solution. The total period of time from excision of the heart to cannulation and perfusion of the artery was less than 4 minutes. Unperfused tissue was carefully removed with a razor blade. The preparation was then placed in a tissue bath and arterially perfused with Tyrode's solution of the following composition (mmol/L): NaCl 129, KCl 4, $NaH_2PO_4$ 0.9, $NaHCO_3$ 20, Ca 1.8, $MgSO_4$ 0.5, glucose 5.5, and insulin 1 U/L, buffered with 95% $O_2$/5% $CO_2$ (36±1° C.). The perfusate was delivered to the artery by a roller pump (Cole Panner Instrument Co). Perfusion pressure was monitored with a pressure transducer (World Precision Instruments, Inc) and maintained between 40 and 50 mm Hg by adjustment of the perfusion flow rate. The preparations remained immersed in the arterial perfusate, which was allowed to rise to a level 2 to 3 mm above the tissue surface (36±1° C.). The results are shown in FIG. 8.

We claim:

1. A method for treating LQT syndrome in a human patient, said method comprising administering to the patient an effective amount of Compound (1) or (2):

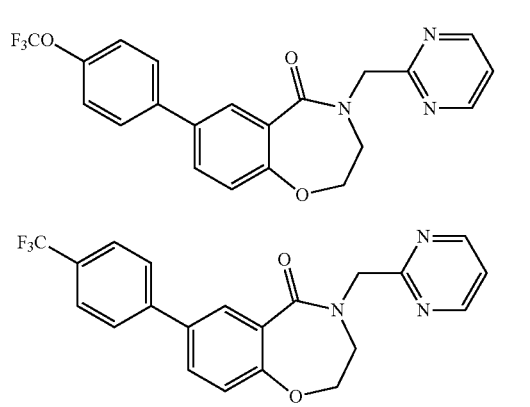

or a pharmaceutically acceptable salt thereof.

2. A method for reducing QTc interval assessed by an echocardiogram or magnetic resonance imaging in a human patient, said method comprising administering to the patient an effective amount of Compound 1 or 2:

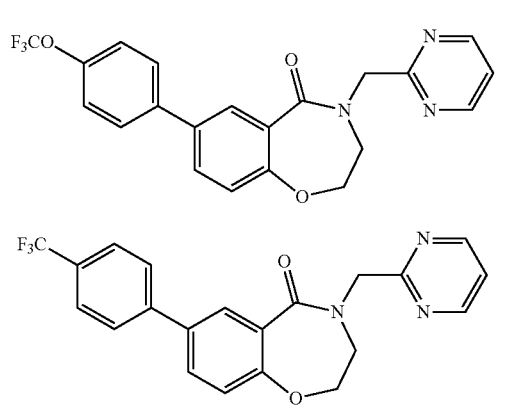

or a pharmaceutically acceptable salt thereof, wherein the QTc interval is caused by a genetic mutation of SCN5A.

3. The method according to claim 1 wherein the compound is

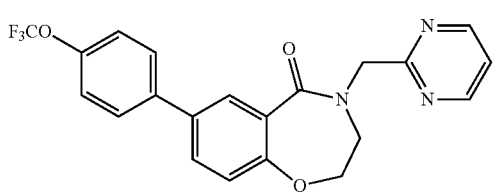

or a pharmaceutically acceptable salt thereof.

4. The method of claim 1 where the compound is

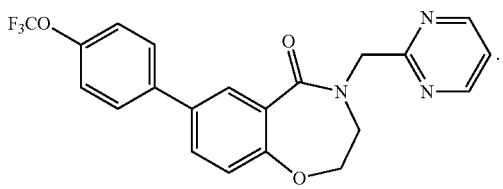

5. The method according to claim 1 wherein the compound is

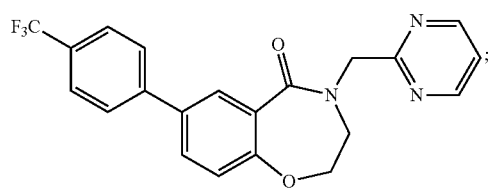

or a pharmaceutically acceptable salt thereof.

6. The method according to claim 1 wherein the compound is

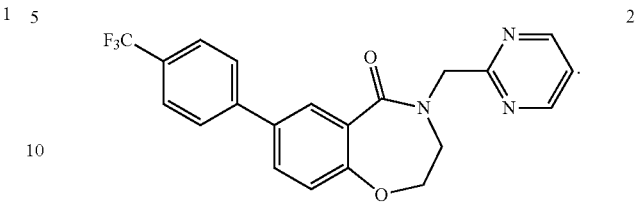

7. The method according to claim 1 or 2, wherein the compound is administered intravenously.

8. The method according to claim 1 or 2, wherein the compound is administered orally.

9. The method according to claim 1 or 2, wherein the effective amount is from about 0.1 mg to about 100 mg per day.

10. The method according to claim 1 or 2, wherein the effective amount is about 1 mg, 3 mg, 6 mg, 9 mg, 10 mg, 12 mg, 18 mg, 20 mg, 30 mg, 40 mg, or 60 mg per day.

11. The method according to claim 1 or 2, wherein the effective amount is about 1 mg, 3 mg, 6 mg, 9 mg, 12 mg and 18 mg per day.

12. The method according to any one of claims 7-11, wherein the compound is administered once a day.

13. The method according to claim 1 wherein the LQT syndrome is LQT3.

14. The method according to claim 1 wherein the LQT syndrome is LQT1 or LQT2.

* * * * *